(12) United States Patent
Hoffman

(10) Patent No.: US 7,687,086 B1
(45) Date of Patent: *Mar. 30, 2010

(54) METHOD FOR OBTAINING TAXANES

(75) Inventor: Angela Marie Hoffman, Beaverton, OR (US)

(73) Assignee: University of Portland, Portland, OR (US)

( * ) Notice: Subject to any disclaimer, the term of this patent is extended or adjusted under 35 U.S.C. 154(b) by 407 days.

This patent is subject to a terminal disclaimer.

(21) Appl. No.: 11/519,310

(22) Filed: Sep. 11, 2006

Related U.S. Application Data

(63) Continuation-in-part of application No. 10/387,700, filed on Mar. 12, 2003, now Pat. No. 7,105,187.

(60) Provisional application No. 60/450,878, filed on Feb. 28, 2003.

(51) Int. Cl.
- *A61K 36/13* (2006.01)
- *C07D 471/00* (2006.01)
- *C07D 487/00* (2006.01)
- *C07D 491/00* (2006.01)
- *C07D 495/00* (2006.01)
- *C07D 497/00* (2006.01)
- *C07D 305/00* (2006.01)
- *C07D 407/00* (2006.01)
- *C07D 493/00* (2006.01)
- *C12P 17/02* (2006.01)

(52) U.S. Cl. ................. 424/770; 544/346; 549/510; 435/123

(58) Field of Classification Search ............... None
See application file for complete search history.

(56) References Cited

U.S. PATENT DOCUMENTS

| | | | |
|---|---|---|---|
| 4,924,011 A | 5/1990 | Denis et al. | |
| 5,279,949 A * | 1/1994 | Nair | 435/123 |
| 5,620,875 A | 4/1997 | Hoffman et al. | |
| 5,620,975 A | 4/1997 | Hoffman et al. | |
| 5,670,663 A | 9/1997 | Durzan et al. | |
| 6,030,818 A * | 2/2000 | Page et al. | 435/123 |
| 6,136,989 A | 10/2000 | Foo et al. | |
| 6,248,572 B1 * | 6/2001 | Choi et al. | 435/123 |
| 6,329,193 B1 | 12/2001 | Strobel et al. | |
| 6,638,742 B1 | 10/2003 | Hoffman | |
| 7,105,187 B1 | 9/2006 | Hoffman | |

FOREIGN PATENT DOCUMENTS

WO   WO 9940989 A1 *   8/1999

OTHER PUBLICATIONS

Appendino, Giovanni et al.; "Taxoids From the Roots of Taxus X Media cv. Hicksii"; Journal of Natural Products; May 1994; vol. 57, No. 5, pp. 607-613.
Chattopadhyay, S.K. et al.; "Studies on the Himalayan Yew Taxus Wallichiana: Part VII—The Taxoids and Phenolic Constituents of the Roots of Taxus Wallichiana"; Indian Journal of Chemistry; Jun. 1999, vol. 33B, pp. 701-704.
Barboni, Luciano et al.; "Taxol Analogues from the Roots of Taxus X Media "; Phytochemistry; 1994; vol. 36, No. 4, pp. 987-990.
Shen, Ya-Ching et al.; "Taxanes from the Roots of Taxus Mairei"; Phytochemistry; 1997; vol. 44, No. 8, pp. 1527-1533.
Shen, Ya-Ching et al.; "New Taxanes Diterpenoids from the Roots of Taxus Mairei"; Journal of Natural Products; 1996; vol. 59, No. 2, pp. 173-176.
Shen, Ya-Ching et al.; "New Taxanes with an Opened Oxetane Ring from the Roots of Taxus Mairei"; Journal of Natural Products; 2000; vol. 63, No. 5, pp. 720-722.
Wickremesinhe, Enaksha R.M. et al.; "Roots of Hydrophonically Grown Taxus Plants as a Source of Taxol and Related Taxanes"; Plant Science; 1994; vol. 101, pp. 125-135.
http://www.science.siu.edu/landplants/Coniferophta/coniferophyta.html, SIUC/Colleg of Science/Land Plants Online Jan. 20, 2000.
http://www.bartleby.com/61/13/S0541300.html, Soil American Heritage Dictionary: 4th Ed 2000.
http://www.biomatnet.org/secure/Fair/F496.htm, Terpenes as Natural Chiral Starting Materials Dec. 1998.

* cited by examiner

*Primary Examiner*—Christopher R Tate
*Assistant Examiner*—Amy L Clark
(74) *Attorney, Agent, or Firm*—Law Office of Karen Dana Oster, LLC

(57) ABSTRACT

A method for obtaining a taxane by which a taxane is isolated from a growth medium, such as soil, pumice, perlite, rocks, and/or gravel in which a taxane-producing plant has grown. A method for obtaining a taxane by which a taxane is isolated from water effluent from plantings of living plants (e.g. a yew tree) that produce a taxane have grown in a growth medium, such as soil, pumice, perlite, rocks, and/or gravel.

5 Claims, 3 Drawing Sheets

US 7,687,086 B1

METHOD FOR OBTAINING TAXANES

The present application is a continuation-in-part of U.S. patent application Ser. No. 10/387,700, filed Mar. 12, 2003, which issued as U.S. Pat. No. 7,105,187 on Sep. 12, 2006. U.S. patent application Ser. No. 10/387,700 is a nonprovisional of U.S. Provisional Patent Application Ser. No. 60/450,878, filed. Feb. 28, 2003. The present application is based on and claims priority from these applications, the disclosures of which are hereby expressly incorporated herein by reference.

BACKGROUND OF INVENTION

The invention pertains to the field of obtaining and isolating physiologically active chemical compounds from natural sources. Specifically, the invention pertains to the field of obtaining and isolating taxanes, including paclitaxel.

Paclitaxel is the active ingredient in the anticancer drug TAXOL® ("taxol") marketed by Bristol-Myers Squibb Company (New York, N.Y.). Taxol has been approved for treatment of ovarian and breast cancers, Kaposi's sarcoma, and non-small-cell lung cancer. It is also in clinical trial for treatment of several other cancers in combination with other chemotherapeutic agents. Several other uses for paclitaxel have been identified, including possible treatments for psoriasis, polycystic kidney disease, multiple sclerosis, and Alzheimer's disease, and for coating stents inserted into blood vessels following angioplasty.

Paclitaxel is a complex diterpenoid compound originally extracted from the bark of the Pacific yew tree, *Taxus brevifolia*. A number of related compounds, collectively known as "taxanes," are also found in the yew extract. Paclitaxel is currently obtained from various species of yew or is made by partial synthesis from other taxanes also obtained from yew. Durzan, U.S. Pat. No. 5,670,663 discloses that taxanes are produced in conifers other than yew, including *Araucaria excelsa, Araucaria angustifolia, Fitzroya cupressoides, Picea abies*, and *Cupressus sempervirens*. In addition to conifers, sources of taxanes have been identified in ginkgo (*Ginkgo biloba*) and hazelnut (*Corylus* spp.) trees.

Strobel, U.S. Pat. No. 6,329,193, incorporated herein by reference, discloses the production of taxanes from fungi and methods of obtaining such fungal-produced taxanes. Several U.S. patents including Foo, U.S. Pat. No. 6,136,989, incorporated herein by reference, disclose methods for extraction of paclitaxel from paclitaxel-containing materials, including from plant tissue and from microorganisms.

Yields of taxanes from these sources are very low, necessitating the continuing search for additional sources of taxanes, especially of taxol.

BRIEF SUMMARY OF THE INVENTION

It has been unexpectedly discovered that one or more taxanes may be obtained from a growth medium, such as soil, in which a living plant that produces a taxane has grown. It has further been unexpectedly discovered that Taxol and one or more other useful taxanes may be obtained from a growth medium, such as pumice, perlite, rocks, and/or gravel, in which a living plant (e.g. a yew tree) that produces a taxane has grown. Still further, it has been unexpectedly discovered that Taxol and one or more other useful taxanes may be extracted from water effluent (run-off) from plantings of living plants (e.g. a yew tree) that produce a taxane grown in a growth medium, such as soil, pumice, perlite, rocks, and/or gravel.

Thus, in one embodiment, the invention is a method for obtaining a taxane from a growth medium (such as soil, pumice, perlite, rocks, and/or gravel) that contains or that has contained a living/growing plant, or a living/growing part of a plant, that produces a taxane. Thus, in another embodiment, the invention is a method for obtaining a taxane from water effluent from plantings of living plants (e.g. a yew tree) that produce a taxane grown in a growth medium, such as soil, pumice, perlite, rocks, and/or gravel.

The foregoing and other objectives, features, and advantages of the invention will be more readily understood upon consideration of the following detailed description of the invention, taken in conjunction with the accompanying drawings.

DETAILED DESCRIPTION OF THE INVENTION

Figure 1:
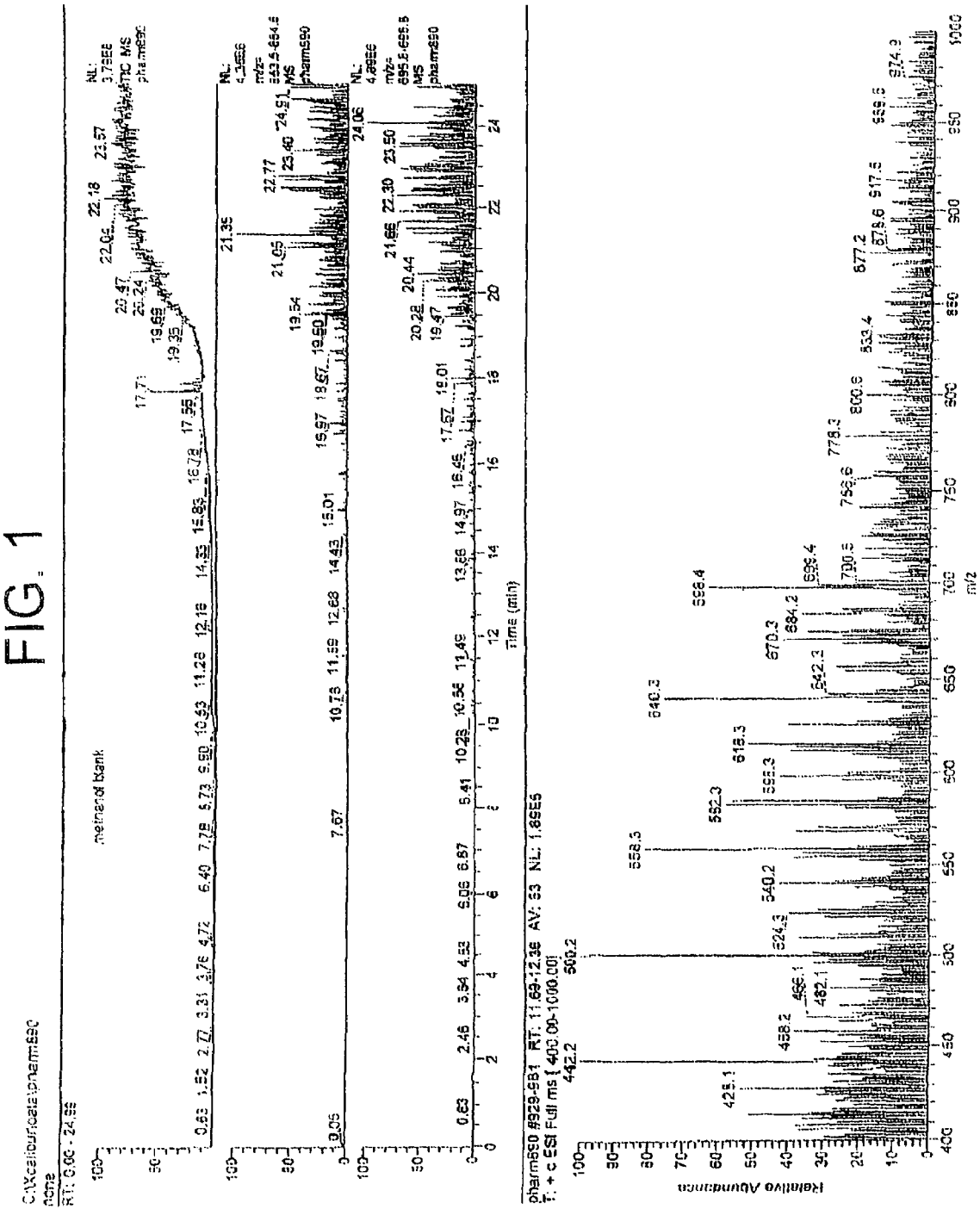
FIG. 1 is a mass spectrograph of a negative control containing a methanol standard and lacking a taxane.
Figure 2:
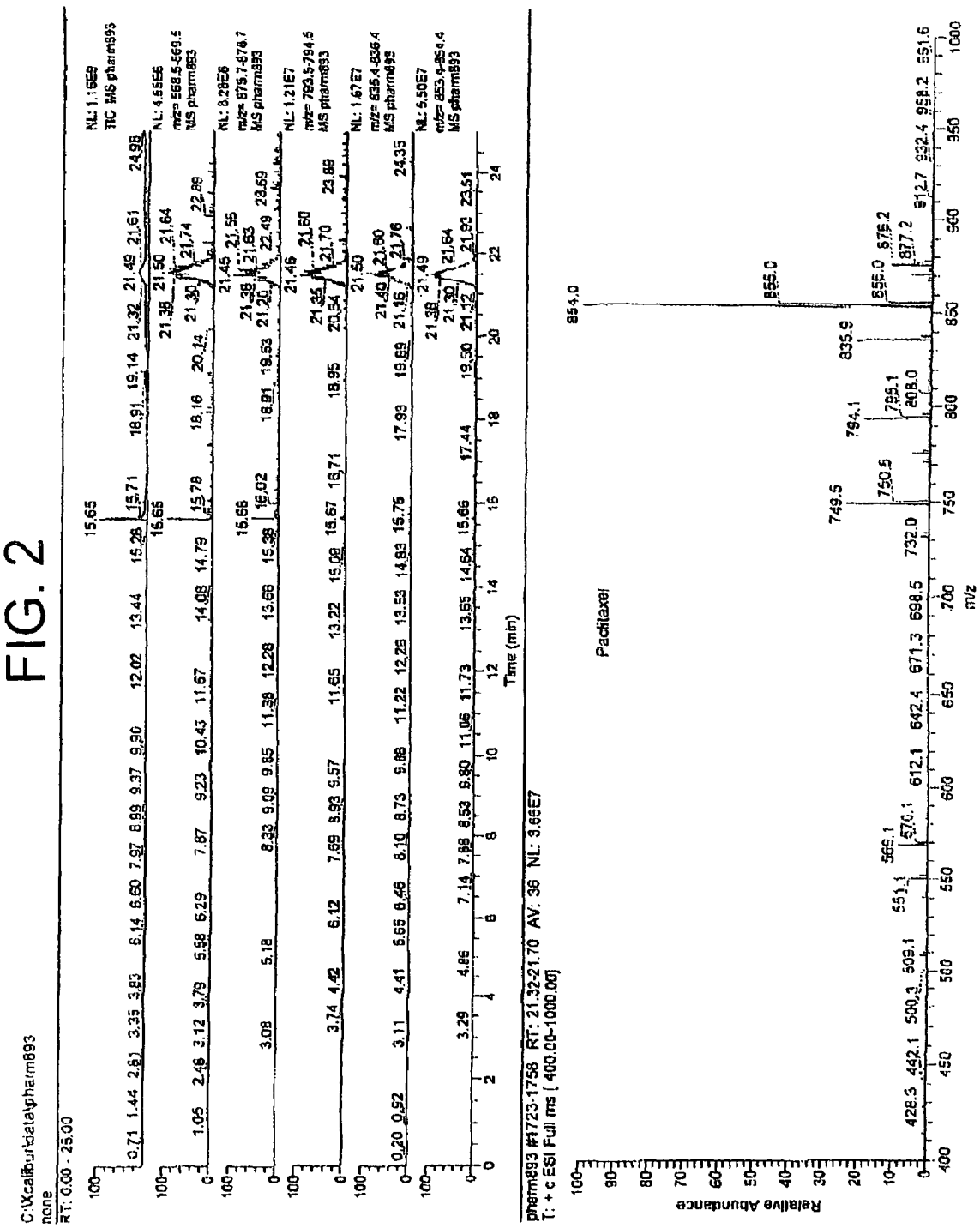
FIG. 2 is a mass spectrograph of a positive control containing taxane, paclitaxel.

"Taxane" means one or all of the taxanes, a known class of chemical compounds some of which may have antitumor properties, whether now known or discovered in the future. The use of any specific taxane, such as "paclitaxel," refers solely to that particular taxane.

"Grow" means to increase either or both in size or number of cells and refers to a complete or whole plant or to a differentiated plant part. A living plant includes at least one root, at least one stem, and at least one leaf.

It has been unexpectedly discovered that a medium in which a taxane-producing plant has grown contains taxanes and that these taxanes may be isolated in order to provide a significant quantity of purified taxane. For example, it has been discovered that the soil in which a taxane-producing plant has grown contains significant quantities of taxane and that the taxane in the soil may be isolated, such as by extraction.

It has further been unexpectedly discovered that Taxol and one or more other useful taxanes may be obtained from a granular growth medium, such as pumice, perlite, rocks, and/or gravel, in which a living plant (e.g. a yew tree) that produces a taxane has grown. Still further, it has been unexpectedly discovered that Taxol and one or more other useful taxanes may be extracted from water effluent from plantings of living plants (e.g. a yew tree) that produce a taxane grown in a growth medium, such as soil, pumice, perlite, rocks, and/or gravel.

These findings have several important consequences. Most important is that, because plants known to produce taxanes produce these taxanes in very small quantities, the discovery that the medium in which such plants have grown contains taxanes provides an additional source from which to obtain these pharmacologically valuable chemical compounds.

The growth medium in which the taxane-producing plants have grown may be a synthetic or a natural medium for growth of such plants. For example, the growth medium may be a synthetic medium, such as Gamborg's B-5 medium (Gamborg, O. L., R. A. Miller and K. Ojima: *Exp. Cell Res.* 50:151 (1968)), Murashige and Skoog medium (Murashige, T. and Skoog, F., *Physiologia Plantarum,* 15:473-97 (1962)), Vacin and Went medium (Vacin, F., and Went, F. W., *Bot. Gaz.* 110:605-613 (1949)), Lloyd and McCown's medium (Lloyd G. and McCown B., Proceedings of the International Plant Propagators' Society 30:421 (1980)), or Phytamax™ medium (Sigma-Aldrich, St. Louis, Mo.). Alternatively, the growth medium may be a soil based medium, including naturally occurring soil, such as topsoil, in which taxane-producing species grow in an uncultivated state. Another alternative growth medium is sand.

Plants that are suitable for the invention include any gymnosperm or angiosperm plant known, or discovered, to produce one or more taxanes. Such plants include but are not limited to yew (*Taxus* spp.), various conifers, hazelnut (*Corylus* spp.), Scotch broom, Red alder, and Huckleberry (*Vacinium parviflorium*).

In accordance with the invention, a growth medium such as soil in which a plant known to produce a taxane has grown is obtained and the taxane is removed and isolated therefrom. The plant may contain all parts normally associated with a plant of the applicable variety, such as roots, stem, leaves, bark, cones, shoots, seeds, nuts, and fruit. Alternatively, the plant may be a part of a plant, such as an explant like a leaf or a shoot, which has grown or is permitted to grow in the growth medium. Preferably, the plant or plant part that is growing in the culture medium and that produces taxane includes a differentiated portion of the plant. That is, in accordance with the invention it is preferable that the plant, or portion thereof, is not solely a callus or cell culture or other undifferentiated plant or plant part.

The taxane may be any presently known or to be discovered taxane. Examples of suitable taxanes include one or more of paclitaxel, cephalomannine, baccatin, taxine, and brevifoliol.

Any method now known in the art or later developed may be utilized in accordance with the invention to obtain taxane from a growth medium in which a taxane-producing plant has grown. For example, the taxane may be obtained by the following process.

The taxane-containing growth medium, which is preferably dried, may be combined, such as by mixing or shaking, with an organic solvent that is suitable for extracting taxanes. Such solvents include methanol, dichloromethane, and ethyl acetate. The solvent containing the taxol is then removed from the mixture, such as by filtration or centrifugation with retention of the filtrate or supernatant. The filtrate or supernatant is then removed from the mixture by evaporation. Strongly hydrophobic components may be extracted and removed with hexane, pentane, or related solvents that are in turn permitted to evaporate. The mixture is then resuspended in ethyl acetate or methanol and is separated by column chromatography, such as HPLC or TLC with, for example, silica gel, and recovered bands are evaluated for the presence of a taxane. Other suitable methods for isolating one or more taxanes that are suitable for the method of the present invention are disclosed in Strobel, U.S. Pat. No. 6,329,193; Foo, U.S. Pat. No. 6,136,989; and Christen, U.S. Pat. No. 5,019,504, each of which is incorporated herein by reference.

The presence of taxane in the growth medium or in a purified sample obtained from a growth medium may be ascertained by any method known or to be discovered. For example, the presence of taxane may be ascertained by a bioassay, such as a brine shrimp bioassay disclosed in Strobel, U.S. Pat. No. 6,329,193.

Alternatively, and preferably, the presence of taxane may be determined by other than a bioassay, such as by spectroscopic analysis. For example, taxane may be determined by an in-vitro tubulin polymerization assay (Vallee, R B, *J. Cell Biol.,* 92:435-442 (1982); Bonham, M J, et al., *J. Natl. Cancer Inst.,* 94:1641-1647 (2002)).

This assay may be performed as follows. 10 microM purified tubulin is incubated with 0.1 M PIPES buffer, pH 6.6 containing 1.0 mM EGTA, 1.0 mM $MgSO_4$, 4% DMSO, 1% paclitaxel or equivalent volume of test solution or ethanol (negative control) for 15 minutes at 30° C. Cool on ice, add 0.4 mM GTP and transfer to a spectrometer cuvette at 4° C. Establish a baseline reading at 4° C. Increase temperature to 30° C. over 60 seconds and incubate for 20 to 30 minutes at 30° C. Measure absorbance at one-minute intervals during this incubation period. Polymerized tubulin increases the absorbance of the solution, which permits the total amount of polymerized tubulin to be estimated for each mixture by plotting absorbance versus time and calculating the area under the curve. Changes of absorbance in test solutions are compared with solutions containing taxol and the negative control.

The invention is further illustrated in the following non-limiting examples. In the examples that follow, the invention is illustrated using extraction of taxane from soil and by production of taxane by yew. It is to be understood that the recitation of soil and yew in the examples is merely illustrative and that any growth medium and any taxane-producing plant may be utilized in accordance with the method of the invention.

EXAMPLE 1

Extraction of Taxanes from Soil

A soil sample was air-dried and all plant matter was removed. Approximately 200 grams of the sample were combined in about 300 ml of methanol and shaken for five minutes or more in order to dissolve taxanes and extract them from the soil sample. The methanol was poured off, filtered, and retained. This step was repeated three times with all the collected methanol from each of the repetitions of the step being pooled.

The methanol was allowed to evaporate and the residue was extracted with hexane in a small amount of water. Because taxanes are not soluble in hexane, the hexane extract was discarded.

The remaining aqueous solution was poured over a C-18 cartridge and components that did not stick to the cartridge were discarded. Components retained on the cartridge were saved and rinsed off the cartridge with methanol. The methanol was evaporated and the residue was weighed and re-dissolved in methanol to a concentration of 50 to 100 micrograms/microliter and then filtered through a 0.2 micron filter to remove particles.

Samples were further separated using a silica gel column in order to remove salts. The filtrate was dissolved in the minimum amount necessary for dissolution in a 1:1 mixture of chloroform and methanol. The solution was eluted through a silica gel column with chloroform with increasing proportions of methanol until the taxane-containing fractions were eluted. These fractions were pooled, evaporated, and dissolved in methanol to a concentration of 50 to 100 micrograms/microliter and filtered to remove particles.

EXAMPLE 2

Separation and Quantification of Taxanes Using HPLC

Components in the solution obtained from Example 1 were separated using high performance liquid chromatography (HPLC). A CUROSIL™ B column (Phenomenex U.S.A., Torrance, Calif.), designed to separate taxanes from a sample, was attached to a Dynamax SD-200 pump system (Rainin Instrument, LLC, Oakland, Calif.) and a Dynamax UV-1 detector (Rainin Instrument, LLC, Oakland, Calif.) set at 228 nm. The solvent system was 45% acetonitrile and 55% ammonium acetate buffer at a pH of 4.0 and a flow rate of 1 ml/min. Retention times for taxanes were compared with those of authentic standards under identical conditions. Calibration curves made by authentic standards were used to quantify compounds eluting at retention times of authentic standards based on their peak areas.

EXAMPLE 3

Identification of Taxanes Using LCMS (Liquid Chromatography Mass Spectroscopy)

Components in the filtered solution were separated by LCMS using a Restek ALLURE™ C-18 column (Restek Corp., Bellefonte, Pa.) attached to a ThermoQuest Finnigan LCQ (Thermo Finnigan, San Jose, Calif.) configured with an electrospray ion source in order to identify the components by mass spectroscopy. Conditions were set as follows: Positive ion mode, ES needle 0.5 to 5.2 kV, ITMS scanned from 120 to 830 amu, full scale with an ion injection of 200 milliseconds.

Figure 3:
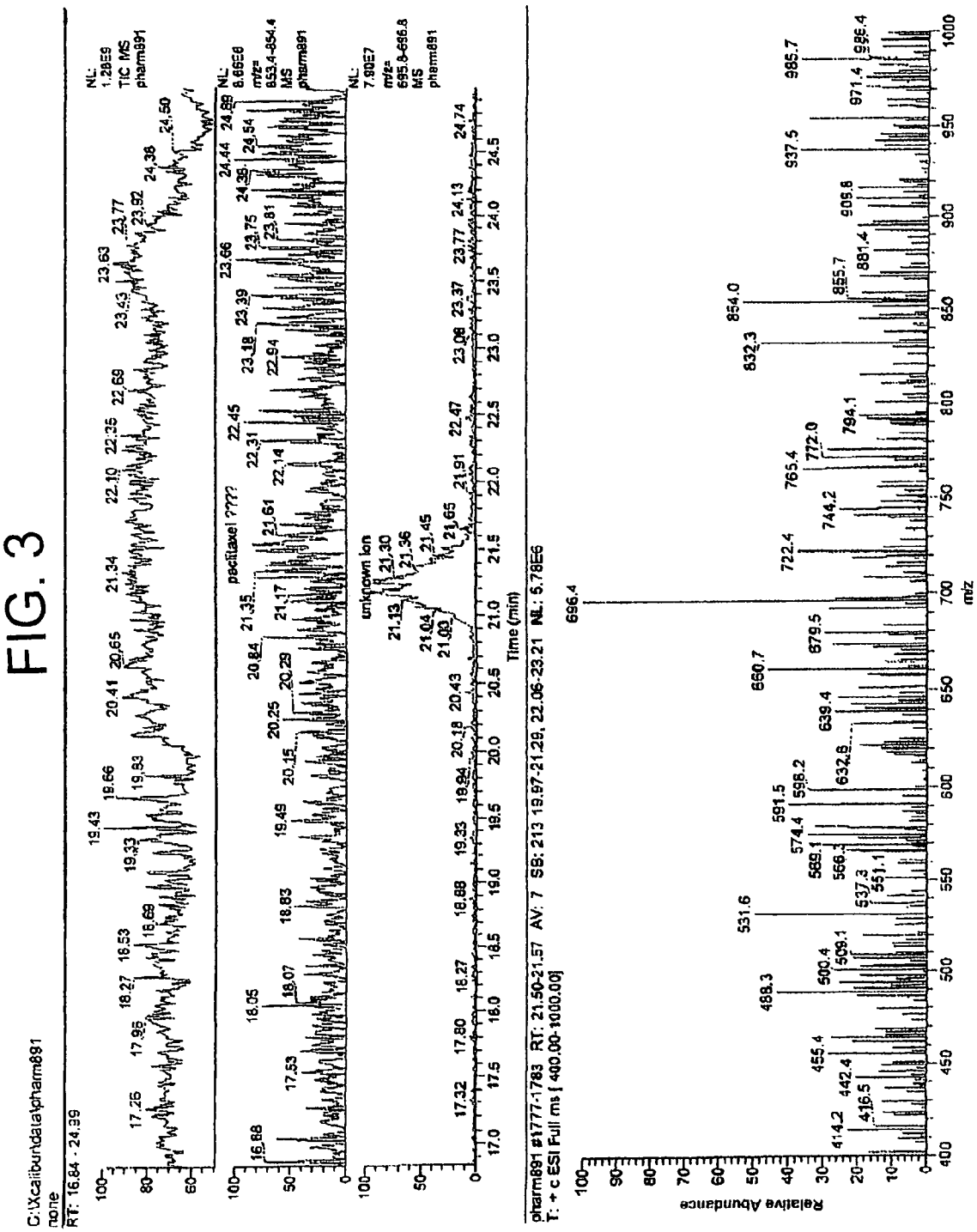
FIG. 3 is a mass spectrograph of a sample prepared in accordance with Examples 1 and 3 showing peaks associated with the presence of one or more taxanes.

As shown in FIG. 3, the mass spectroscopy of soil samples processed in accordance with Examples 1 and 2 showed peaks at 854, 794, 569, and 551, indicative of the presence of paclitaxel in the samples. Additionally, peaks at 832 and 772 confirmed the presence of cephalomannine in the samples.

EXAMPLE 4

Extraction of Taxanes from Granular Growth Mediums

The following is an example of an extraction procedure for removing (extracting) taxanes from granular growth medium material in which a living plant (e.g. a yew tree) that produces at least one taxane has grown. Satisfactory test results have been obtained in tests in which the living plant has grown for ten weeks in the granular growth medium (see Table 1) and in which the living plant has grown for nine months in the granular growth medium.

TABLE 1

Six different taxanes extracted from perlite after six 7- to 8-inch yew trees were grown for ten weeks.

| Taxane | $\mu g/ft^3$ of perlite |
| --- | --- |
| 10 deacetyl Baccatin III | 90.55 |
| Baccatin III | 122.23 |
| 10 deacetyl Taxol | 127.01 |
| Cephalomannine | 1,343.22 |
| 7 epi, 10 deacetyl Taxol | 138.78 |
| Paclitaxel | 202.50 |

Granular growth medium is preferably a medium having a plurality of grains (preferably water insoluble), the grains having an average diameter of more than 0.5 mm. In preferred embodiments the grains of the granular growth medium would have an average diameter of more than 2 mm. It should be noted that exemplary granular growth medium may include pumice, perlite (a naturally occurring siliceous rock), rocks, gravel, etc.

The granular growth medium is collected, preferably partially dried, and placed into the mixer with enough solvent so it is thoroughly wet. It should be noted that the solvent could be an alcohol such as methanol or isopropyl alcohol or it could be another solvent such as dichloromethane or chloroform. The wet growth medium is then mixed such as by agitating, shaking, or stirring. Test results for mixing one or more hours and for mixing overnight have yielded satisfactory results. The solvent is then separated or removed from the mixture by methods such as by filtering or centrifugation.

The steps of wetting the granular growth medium with solvent, mixing the mixture, and separating are preferably repeated (e.g. two more times) using fresh or recycled solvent. Test results have shown that repeating the extraction increases the yield significantly. In one test, the yield was more than doubled.

The resulting product of the multiple separations is preferably concentrated and purified. One or more of these steps may be skipped if the granular growth medium was reasonably dry.

Concentration may be accomplished by evaporating solvent from the resulting product of the multiple separations. A rotary-evaporator may be used for the evaporating step. After evaporation, a small amount of liquid remaining is likely to be water.

Purification is the process of removing water-soluble compounds such as water, salts, fertilizers and other impurities. Purification may be accomplished, for example, by adding an equal portion of water to the resulting product of the multiple filterings and running it over a C-18 column using vacuum. The taxanes are removed from the C-18 column using an appropriate solvent. It should be noted that purification may be accomplished using L-H20 or other relevant matrices.

If necessary to obtain a satisfactorily concentrated and dried product, the solvent may be evaporated again and any remaining water may be removed by freeze drying.

The concentrated and/or purified product (residue) is dissolved in a small portion of solvent and prepared for quantification by HPLC (high performance liquid chromatography) or other type of chromatography. Alternatively, a more concentrated sample may be purified by HPLC such as on a preparative column.

A procedure may be used to verify that the collected fraction (the taxanes collected) is authentic and/or to assess its purity. An HPLC-MS may be used for this purpose.

EXAMPLE 5

Extraction of Taxanes from Water

The following is an example of an extraction procedure for removing (extracting) taxanes from effluent (run-off) from growth medium material (e.g. soil, pumice, perlite, rocks, and/or gravel, etc.) in which a living plant (e.g. a yew tree) that produces at least one taxane has grown. Satisfactory test results have been obtained in tests in which the living plant has grown for ten weeks in the granular growth medium (see Table 2) and in which the living plant has grown for nine months in the granular growth medium.

TABLE 2

Six different taxanes extracted from effluent water used to irrigate six 7- to 8-inch yew trees, pro-rated per month.

| Taxane (ug/ft³) | (μg/month) |
|---|---|
| 10 deacetyl Baccatin III | 1.54 |
| Baccatin III | 3.50 |
| 10 deacetyl Taxol | 4.53 |
| Cephalomannine | 1.99 |
| 7 epi, 10 deacetyl Taxol | 0.71 |
| Paclitaxel | 2.91 |

In this exemplary procedure, effluent is collected from the growth medium material in which at least one living plant that produces a taxane has grown. The effluent (e.g. water) is pumped through a matrix such as C-18, Amberlite XAD, or other product which will adsorb the taxanes. The matrix is then rinsed well with plain water (e.g. filtered water, purified water, or even regular tap water) to remove impurities (e.g. salts).

The matrix is then rinsed with a solvent that will dissolve taxanes. It should be noted that the solvent could be an alcohol such as methanol or isopropyl alcohol or it could be another solvent such as dichloromethane or chloroform. The solvent is evaporated leaving the residue containing taxanes.

The concentrated and/or purified product (residue) is dissolved in a small portion of solvent and prepared for quantification by HPLC (high performance liquid chromatography) or other type of chromatography. Alternatively, a more concentrated sample may be purified by HPLC such as on a preparative column.

A procedure may be used to verify that the collected fraction (the taxanes collected) is authentic and/or to assess its purity. An HPLC-MS may be used for this purpose.

All articles and patents cited in this application are incorporated herein by reference.

Further modifications, uses, and applications of the invention described herein will be apparent to those skilled in the art. It is intended that such modifications be encompassed in the claims that follow.

The terms and expressions that have been employed in the foregoing specification are used as terms of description and not of limitation, and are not intended to exclude equivalents of the features shown and described or portions of them. The scope of the invention is defined and limited only by the claims that follow.

What is claimed is:

1. A method for obtaining one or more taxanes from a sample comprising:
    (a) obtaining effluent from a water insoluble growth medium in which a taxane-producing complete living plant or differentiated plant part has grown; and
    (b) isolating the taxane from said effluent.

2. The method of claim 1 wherein said growth medium is selected from the group consisting of:
    (a) soil;
    (b) pumice;
    (c) perlite;
    (d) rocks; and
    (e) gravel.

3. The method of claim 1 wherein the taxane-producing plant is selected from the group consisting of:
    (a) a yew;
    (b) yew (*Taxus* spp.);
    (c) hazelnut (*Corylus* spp.); and
    (d) a conifer.

4. The method of claim 1 wherein the taxane is selected from the group consisting of:
    (a) paclitaxel;
    (b) cephalomannine;
    (c) baccatin;
    (d) brevifoliol; and
    (e) deacetyl taxanes.

5. The method of claim 1 wherein the taxane is obtained by chromatography.

* * * * *